United States Patent [19]
Guram et al.

[11] Patent Number: 6,124,476
[45] Date of Patent: Sep. 26, 2000

[54] CATALYST LIGANDS, CATALYST COMPOSITIONS, CATALYST METAL COMPLEXES AND PROCESSES FOR CROSS-COUPLING AROMATIC BORON COMPOUNDS WITH AROMATIC HALOGENS OR PERFLUOROALKYLSULFONATES

[75] Inventors: Anil Guram, Cupertino; Xiaohong Bei, San Jose; Timothy S. Powers, San Francisco; Bernd Jandeleit, Palo Alto; Thomas Crevier, San Jose, all of Calif.

[73] Assignee: Symyx Technologies, Inc., Santa Clara, Calif.

[21] Appl. No.: 09/252,182

[22] Filed: Feb. 18, 1999

Related U.S. Application Data

[63] Continuation-in-part of application No. 09/062,128, Apr. 17, 1998
[60] Provisional application No. 60/095,612, Aug. 6, 1998.
[51] Int. Cl.[7] .................... C07D 321/00; C07D 307/02; C07F 15/00; C07F 9/02
[52] U.S. Cl. .................... 549/200; 549/491; 549/497; 556/18; 556/21; 556/136; 556/146; 562/493; 562/504; 568/2; 568/6; 568/13; 568/17
[58] Field of Search .................... 549/200, 491, 549/497; 568/2, 6, 13, 17; 556/18, 21, 136, 146; 562/504, 493

[56] References Cited

FOREIGN PATENT DOCUMENTS

| | | |
|---|---|---|
| 2239970A | 6/1997 | Canada . |
| WO 93/12260 | 6/1993 | WIPO . |
| WO 99/54337 | 10/1999 | WIPO . |

OTHER PUBLICATIONS

Chemical Abstract vol. 131, 1999 12–07 No. 2 (abstract of Organmetallics, 1999 18 (10) 1840–1853).
Chemical Abstract vol. 124 (1996) 09–04 No. 15 (abstract of Bull. Korean Chem. Soc. 1995 16(12) 1135–8.).
Shirakawa E., May 26, 1997, Tetrahedron Letters 38 (21): 759–3762 "An Iminophosphine–palladium catalyst for cross–coupling of aryl halides with organostannanes".
Horner, L., 1984, Zeitschrift Fur Naturforschung, Teil B : Anorganische Chemie, Organische Chemie., 39 (4) : 504–511 "Tertiare Phosphine mit Ortho–standigen chelatisierungsfahigen funktionellen Gruppen als Co–Katalysatoren der Homogenhydrierung mit Rh(l)–Komplexen".
Trofimov B.A., 1995, Synthesis 4: 387–388 "Base–catalyzed addition of phosphine to aryl–and hetarylethynes".
Kamikawa, K., Nov. 13, 1998, J. Org. Chem. 63 (23): 8407–8410 "Palladium–Catalyzed Amination of Ayrl Bromides Utilizing Arene–Chromium Complexes as Ligands".
Bei, Xiaohong et al., 1999, Tetrahederon Letters 40: 1237–1240 General and Efficient Palladium–Catalyed Aminations of Aryl Chlorides.
Schiemenz, Günter P., et al., "Aromatic phosphines with second order substituents. XIII. Preparation of triarylphosphines with several carbonyl functions by Grignard synthesis," Liebigs. Ann. Chem., vol. 9, pp. 1480–1493, 1973.
Hellwinkel, Dieter., et al., "Polycyclic triaryldioxyphosphoranes of extreme stability," Chem. Bur., vol. 111, pp. 13–41, 1978.
Hoots, John E., et al., "Substituted triaryl phosphines," Inorg. Synth., vol. 21, pp. 175–179, 1982.
Vaughn, George D., et al., "Synthesis and reactivity of stable metallacyclic manganese and rhenium α–hydroxyalkyl complexes of the formula [cyclic] $(CO)_4MP(C_6H_5)_2(o-C_6H_4CHOH)$," J. Am. Chem. Soc., vol. 108, pp. 1462–1473, 1986.
Frost, Christopher G., et al., "Enantiomerically pure acetals as ligands for asymmetric catalysis," Synlett, Issue 7, pp. 551–552, 1994.
Newman, Louise M., et al., "Rhodium catalysed asymmetric hydrosilylation of ketones using phosphorus–containing oxazoline ligands," Tetrahedron: Asymmetry, vol. 7, No. 6, pp. 1597–1598, 1996.
Grotjahn D.B., et al., "Ruthenium alkoxycarbene complexes from an acetal function by C–O bond cleavage and alcohol elimination," Organometallics, vol. 15, pp. 2860–2862, 1996.
Xu, Pian–pian, et al., "Synthesis, structure and hydrogenation property of trans–$PdCl_2\{Ph_2P[o-C_6H_4CH(OC_2H_5)_2]\}_2$," Chem. Res. Chin. Univ., vol. 13, No. 4, pp. 397–400, 1997.
Xu, Pian–pian, et al., "Synthesis, characterization of new palladium complexes and their catalytic properties in hydrogenation reaction," Journal of Xiamen University, vol. 37, No. 1, pp. 52–57, 1998.

Primary Examiner—Porfirio Nazario-Gonzalez

[57] ABSTRACT

The present invention discloses new organic compounds (e.g., ligands), their metal complexes and compositions using those compounds. The invention also relates to the field of catalysis. In particular, this invention relates to new compounds which when combined with suitable metals or metal precursor compounds provide useful catalysts for various bond-forming reactions, including Suzuki cross-coupling reactions. The invention also relates to performing Suzuki cross coupling reactions with unreactive arylchlorides.

30 Claims, No Drawings

CATALYST LIGANDS, CATALYST COMPOSITIONS, CATALYST METAL COMPLEXES AND PROCESSES FOR CROSS-COUPLING AROMATIC BORON COMPOUNDS WITH AROMATIC HALOGENS OR PERFLUOROALKYLSULFONATES

This application is a continuation-in-part of U.S. patent application Ser. No. 09/062,128, filed Apr. 17, 1998, the disclosure of which is incorporated herein by reference. This application also claims the benefit of U.S. Provisional Application Ser. No. 60/095,612, filed Aug. 6, 1998, the disclosure of which is incorporated herein by reference.

FIELD OF THE INVENTION

The present invention relates to new organic compounds (e.g., ligands), their metal complexes and compositions using those compounds; the invention also relates to the field of catalysis. In particular, this invention relates to new compounds which when combined with suitable metals or metal precursor compounds provide useful catalysts for various bond-forming reactions, including Suzuki cross-coupling reactions. The invention also relates to a process for preparing polycyclic aromatic compounds by a cross-coupling reaction of suitable aromatic nucleophiles and suitable aromatic electrophiles catalyzed by the novel compositions or metal complexes.

BACKGROUND OF THE INVENTION

Ancillary (or spectator) ligand-metal coordination complexes (e.g., organometallic complexes) and compositions are useful as catalysts, additives, stoichiometric reagents, monomers, solid state precursors, therapeutic reagents and drugs. Ancillary ligand-metal coordination complexes of this type can be prepared by combining an ancillary ligand with a suitable metal compound or metal precursor in a suitable solvent under suitable reaction conditions. The ancillary ligand may contain functional groups that bind to the metal center(s), remain associated with the metal center (s), and therefore provide an opportunity to modify the steric, electronic and chemical properties of the active metal center(s) of the complex.

Certain known ancillary ligand-metal complexes and compositions are catalysts for reactions such as oxidation, reduction, hydrogenation, hydrosilylation, hydrocyanation, hydroformylation, polymerization, carbonylation, isomerization, metathesis, carbon-hydrogen activation, carbon-halogen activation, cross-coupling, hetero cross-coupling, Friedel-Crafts acylation and alkylation, hydration, amination, aryl amination, dimerization, trimerization, oligomerization, Diels-Alder reactions and other transformations.

One example of the use of these types of ancillary ligand-metal complexes and compositions is in the field of cross-coupling reactions. The palladium-catalyzed cross-coupling reactions of aryl-chlorides, bromides, iodides, and triflates with alkyl or aryl-boron compounds provide a general and efficient route to a wide variety of substituted alkylphenyl or biphenyl compounds, and have now been extensively developed. See Suzuki, A. in *Metal-Catalyzed Cross-Coupling Reactions*; Diederich, F., Stang, P. J., Eds.; Wiley-VCH: Weinheim, Germany, 1998; Chapter 2, pp. 49–97, which is incorporated herein by reference. See also U.S. Pat. Nos. 5,550,236 and 5,756,804, both of which are incorporated herein by reference.

However, the related palladium-catalyzed reactions of the comparatively inexpensive and readily available aryl chlorides, which represent the most attractive candidates for industrial applications of these reactions, have been under-developed. See Old, D. W., Wolfe, J. P., Buchwald, S. L., *J. Am. Chem. Soc.* 1998, 120, 9722–9723; and Littke, A. F., Fu, G. C., *Angew. Chem. Int. Ed. Eng.* 1998, 37, 3387–3388, which are both incorporated herein by reference.

This invention provides a new, general, and efficient catalyst for cross-coupling reactions in general and more specifically for the Suzuki reaction between aryl halides, especially relatively unreactive aryl chlorides, with alkyl and aryl-substituted boronic acid derivatives and aryl-substituted perfluoroalkylsulfonates. Compounds prepared according to the invention are suitable for use as precursors for pharmaceuticals, cosmetics, fungicides, herbicides, dyes, detergents, and polymers, including additives for these. Compounds prepared according to the invention are, in particular, valuable precursors for angiotensin II inhibitors. See *Drugs of the Future* 1993, 18, 428–432.

SUMMARY OF THE INVENTION

Thus, it is an object of this invention to provide novel ligands for use in catalyzing a chemical transformation. These ligands are typically included either in a catalytic composition additionally including a metal precursor or a metal complex. In a first aspect, the invention disclosed herein is a ligand (i.e., an ancillary ligand), which can be characterized by either of the general formulas:

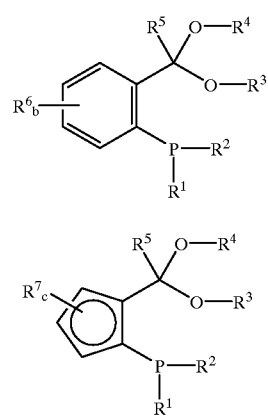

wherein each $R^1$ and $R^2$ is independently selected from the group consisting of alkyl, substituted alkyl, cycloalkyl and substituted cycloalkyl.

Each of $R^3$, $R^4$ and $R^5$ is independently selected from the group consisting of hydrogen, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, metallocene and combinations thereof; and b is 0, 1, 2, 3 or 4; c is 0, 1, 2 or 3 and optionally, $R^3$ and $R^4$ are joined together in a ring structure. Each $R^6$ and $R^7$ is independently selected from the same group as $R^5$, but may additionally be a water solubilizing group or a transition metal. Also optionally two or more $R^6$ or $R^7$ groups are joined together in a ring structure. In connection with formula II, $R^7$ will typically be a transition metal containing moiety so that formula II may, for example, be a bis-cyclopentadienyl metallocene.

In a second aspect, the invention disclosed herein is a ligand that can be characterized by the general formula:

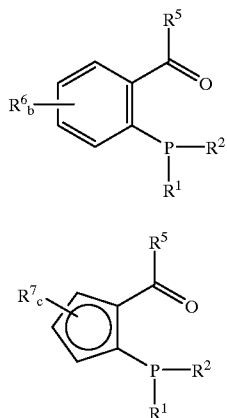

III

IV wherein $R^1$, $R^2$, $R^5$, $R^6$, $R^7$, b and c have the definitions given above.

The ligands of this invention are added to a metal precursor to provide a catalytic composition or new metal-ligand complexes. And, it is an object of this invention to provide new compositions comprising the new ligand and a metal precursor and new metal complexes. For catalysis, the ligands from the above two aspects can be included in a composition including a suitable metal or metal precursor compound that can be of the form $ML_n$, where the composition has catalytic properties. Also, the ligands can be coordinated with a metal precursor to form metal-ligand complexes, which may be catalysts. Here, M is a transition metal selected from the group consisting of Groups 5, 6, 7, 8, 9 and 10 of the Periodic Table of Elements, preferably Pd, Ni, Ru, Rh, Pt, Co, Ir and Fe; L is independently each occurrence, a neutral and/or charged ligand; and n is a number 0, 1, 2, 3, 4, and 5, depending on M.

Another aspect of this invention is the chemical transformations that the new catalytic compositions or metal complexes enhance, and it is an object of this invention to provide catalysts and methods for such transformations. The compositions and metal complexes are useful as catalysts for various chemical transformations, particularly cross coupling transformations. Specifically, the preparation of polycyclic aromatic compounds by a cross-coupling reaction of a first aromatic compound and second aromatic compound, more specifically with aromatic boron compounds and aromatic halogen compounds or perfluoroalkylsulfonates may be performed, and it is an object of this invention to provide catalysts and methods for such cross coupling reactions. The benefit of using these catalysts in such reactions is generally higher conversions (e.g., turnovers) when using less costly starting materials.

Further aspects of this invention will be evident to those of skill in the art upon review of this specification.

DETAILED DESCRIPTION OF THE INVENTION

The invention disclosed herein is new ligands that may be combined with metals or metal precursor compounds to form coordination complexes or compositions of matter, which are useful as catalysts for chemical reactions, as well as processes for making the ligand and using the resultant composition or coordination complex as a catalyst. This invention supplements U.S. patent application Ser. No. 09/062,128, incorporated herein by reference. In addition, this invention was made with combinatorial techniques. See Danielson, E., Golden, J. H., McFarland, E. W., Reaves, C. M., Weinberg, W. H., Wu, X. D. *Nature* 1997, 389, 944–1948 and U.S. patent application Ser. No. 08/898,715, filed Jul. 22, 1997, both of which are incorporated herein by reference. For recent general reviews on combinatorial catalysis, see Weinberg, W. H., Jandeleit, B., Self, K.; Turner, H. *Curr. Opin. Solid State Mater. Sci.* 1998, 3, 104–110 and Gennari, C., Nestler, H. P., Piarulli, U., Salom, B. *Liebigs Ann./Recueil* 1997, 637–647, both of which are incorporated herein by reference.

As used herein, the phrase "characterized by the formula" is not intended to be limiting and is used in the same way that "comprising" is commonly used. The term "independently selected" is used herein to indicate that the R groups, e.g., $R^1$, $R^2$, $R^3$, $R^4$, $R^5$ and $R^6$ can be identical or different (e.g. $R^1$, $R^2$ and $R^3$ may all be substituted alkyls or $R^1$ and $R^2$ may be a substituted alkyl and $R^3$ may be an aryl, etc.). A named R group will generally have the structure that is recognized in the art as corresponding to R groups having that name. For the purposes of illustration, representative R groups as enumerated above are defined herein. These definitions are intended to supplement and illustrate, not preclude, the definitions known to those of skill in the art.

The term "alkyl" is used herein to refer to a branched or unbranched, saturated or unsaturated acyclic hydrocarbon radical. Suitable alkyl radicals include, for example, methyl, ethyl, n-propyl, i-propyl, 2-propenyl (or allyl), vinyl, n-butyl, t-butyl, i-butyl (or 2-methylpropyl), etc. In particular embodiments, alkyls have between 1 and 200 carbon atoms, between 1 and 50 carbon atoms or between 1 and 20 carbon atoms.

"Substituted alkyl" refers to an alkyl as just described in which one or more hydrogen atom to any carbon of the alkyl is replaced by another group such as a halogen, aryl, substituted aryl, cycloalkyl, substituted cycloalkyl, and combinations thereof. Suitable substituted alkyls include, for example, benzyl, trifluoromethyl and the like.

The term "heteroalkyl" refers to an alkyl as described above in which one or more hydrogen atoms to any carbon of the alkyl is replaced by a heteroatom selected from the group consisting of N, O, P, B, S, Si, Se and Ge. The bond between the carbon atom and the heteroatom may be saturated or unsaturated. Thus, an alkyl substituted with a heterocycloalkyl, substituted heterocycloalkyl, heteroaryl, substituted heteroaryl, alkoxy, aryloxy, boryl, phosphino, amino, silyl, thio, or seleno is within the scope of the term heteroalkyl. Suitable heteroalkyls include cyano, benzoyl, 2-pyridyl, $^2$-furyl and the like.

The term "cycloalkyl" is used herein to refer to a saturated or unsaturated cyclic non-aromatic hydrocarbon radical having a single ring or multiple condensed rings. Suitable cycloalkyl radicals include, for example, cyclopentyl, cyclohexyl, cyclooctenyl, bicyclooctyl, etc. In particular embodiments, cycloalkyls have between 3 and 200 carbon atoms, between 3 and 50 carbon atoms or between 3 and 20 carbon atoms.

"Substituted cycloalkyl" refers to cycloalkyl as just described including in which one or more hydrogen atom to any carbon of the cycloalkyl is replaced by another group such as a halogen, alkyl, substituted alkyl, aryl, substituted aryl, cycloalkyl, substituted cycloalkyl, heterocycloalkyl, substituted heterocycloalkyl, heteroaryl, substituted heteroaryl, alkoxy, aryloxy, boryl, phosphino, amino, silyl, thio, seleno and combinations thereof. Suitable substituted cycloalkyl radicals include, for example, 4-dimethylaminocyclohexyl, 4,5-dibromocyclohept-4-enyl, and the like.

The term "heterocycloalkyl" is used herein to refer to a cycloalkyl radical as described, but in which one or more or all carbon atoms of the saturated or unsaturated cyclic radical are replaced by a heteroatom such as nitrogen, phosphorous, oxygen, sulfur, silicon, germanium, selenium, or boron. Suitable heterocycloalkyls include, for example, piperazinyl, morpholinyl, tetrahydropyranyl, tetrahydrofuranyl, piperidinyl, pyrrolidinyl, oxazolinyl, and the like.

"Substituted heterocycloalkyl" refers to heterocycloalkyl as just described including in which one or more hydrogen atom to any atom of the heterocycloalkyl is replaced by another group such as a halogen, alkyl, substituted alkyl, aryl, substituted aryl, heteroaryl, substituted heteroaryl, alkoxy, aryloxy, boryl, phosphino, amino, silyl, thio, seleno and combinations thereof. Suitable substituted heterocycloalkyl radicals include, for example, N-methylpiperazinyl, 3-dimethylaminomorpholine, and the like.

The term "aryl" is used herein to refer to an aromatic substituent which may be a single aromatic ring or multiple aromatic rings which are fused together, linked covalently, or linked to a common group such as a methylene or ethylene moiety. The common linking group may also be a carbonyl as in benzophenone or oxygen as in diphenylether or nitrogen in diphenylamine. The aromatic ring(s) may include phenyl, naphthyl, biphenyl, diphenylether, diphenylamine and benzophenone among others. In particular embodiments, aryls have between 1 and 200 carbon atoms, between 1 and 50 carbon atoms or between 1 and 20 carbon atoms.

"Substituted aryl" refers to aryl as just described in which one or more hydrogen atom to any carbon is replaced by one or more functional groups such as alkyl, substituted alkyl, cycloalkyl, substituted cycloalkyl, heterocycloalkyl, substituted heterocycloalkyl, halogen, alkylhalos (e.g., $CF_3$), hydroxy, amino, phosphino, alkoxy, amino, thio and both saturated and unsaturated cyclic hydrocarbons which are fused to the aromatic ring(s), linked covalently or linked to a common group such as a methylene or ethylene moiety. The linking group may also be a carbonyl such as in cyclohexyl phenyl ketone.

The term "heteroaryl" as used herein refers to aromatic rings in which one or more carbon atoms of the aromatic ring(s) are replaced by a heteroatom(s) such as nitrogen, oxygen, boron, selenium, phosphorus, silicon or sulfur. Heteroaryl refers to structures that may be a single aromatic ring, multiple aromatic ring(s), or one or more aromatic rings coupled to one or more nonaromatic ring(s). In structures having multiple rings, the rings can be fused together, linked covalently, or linked to a common group such as a methylene or ethylene moiety. The common linking group may also be a carbonyl as in phenyl pyridyl ketone. As used herein, rings such as thiophene, pyridine, isoxazole, phthalimide, pyrazole, indole, furan, etc. or benzo-fused analogues of these rings are defined by the term "heteroaryl."

"Substituted heteroaryl" refers to heteroaryl as just described including in which one or more hydrogen atoms to any atom of the heteroaryl moiety is replaced by another group such as a halogen, alkyl, substituted alkyl, aryl, substituted aryl, heteroaryl, substituted heteroaryl, alkoxy, aryloxy, boryl, phosphino, amino, silyl, thio, seleno and combinations thereof. Suitable substituted heteroaryl radicals include, for example, 4-N,N-dimethylaminopyridine.

The term "alkoxy" is used herein to refer to the $—OZ^1$ radical, where $Z^1$ is selected from the group consisting of alkyl, substituted alkyl, cycloalkyl, substituted cycloalkyl, heterocylcoalkyl, substituted heterocycloalkyl, silyl groups and combinations thereof as described herein. Suitable alkoxy radicals include, for example, methoxy, ethoxy, benzyloxy, t-butoxy, etc. A related term is "aryloxy" where $Z^1$ is selected from the group consisting of aryl, substituted aryl, heteroaryl, substituted heteroaryl, and combinations thereof. Examples of suitable aryloxy radicals include phenoxy, substituted phenoxy, 2-pyridinoxy, 8-quinalinoxy and the like.

As used herein the term "silyl" refers to the $—SiZ^1Z^2Z^3$ radical, where each of $Z^1$, $Z^2$, and $Z^3$ is independently selected from the group consisting of alkyl, substituted alkyl, cycloalkyl, heterocycloalkyl, heterocyclic, aryl, substituted aryl, heteroaryl, substituted heteroaryl, alkoxy, aryloxy, amino, silyl and combinations thereof.

As used herein the term "boryl" refers to the $—BZ^1Z^2$ group, where each of $Z^1$ and $Z^2$ is independently selected from the group consisting of alkyl, substituted alkyl, cycloalkyl, heterocycloalkyl, heterocyclic, aryl, substituted aryl, heteroaryl, substituted heteroaryl, alkoxy, aryloxy, amino, silyl and combinations thereof.

As used herein, the term "phosphino" refers to the group $—PZ^1Z^2$, where each of $Z^1$ and $Z^2$ is independently selected from the group consisting of hydrogen, substituted or unsubstituted alkyl, cycloalkyl, heterocycloalkyl, heterocyclic, aryl, heteroaryl, silyl, alkoxy, aryloxy, amino and combinations thereof.

The term "amino" is used herein to refer to the group $—NZ^1Z^2$, where each of $Z^1$ and $Z^2$ is independently selected from the group consisting of hydrogen; alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, silyl and combinations thereof.

The term "thio" is used herein to refer to the group $—SZ^1$, where $Z^1$ is selected from the group consisting of hydrogen; alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, silyl and combinations thereof.

The term "seleno" is used herein to refer to the group $—SeZ^1$, where $Z^1$ is selected from the group consisting of hydrogen; alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, silyl and combinations thereof.

The term "saturated" refers to lack of double and triple bonds between atoms of a radical group such as ethyl, cyclohexyl, pyrrolidinyl, and the like.

The term "unsaturated" refers to the presence one or more double and triple bonds between atoms of a radical group such as vinyl, acetylenyl, oxazolinyl, cyclohexenyl, acetyl and the like.

The ancillary ligands of this invention can be characterized by either of the general formulas:

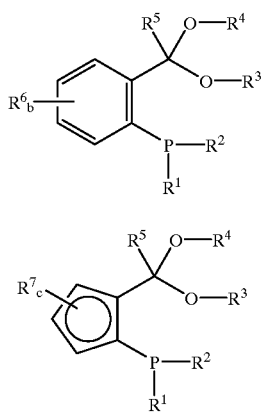

wherein each $R^1$ and $R^2$ is independently selected from the group consisting of alkyl, substituted alkyl, cycloalkyl and substituted cycloalkyl; and each of $R^3$, $R^4$ and $R^5$ is independently selected from the group consisting of hydrogen, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, and combinations thereof; and optionally, $R^3$ and $R^4$ are joined together in a ring structure; also optionally two or more $R^6$ groups are joined together in a ring structure;

each $R^6$ and $R^7$ is independently selected from the group consisting of hydrogen, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, water solubilizing groups, transition metals and combinations thereof; b is 0, 1, 2, 3 or 4; and c is 0, 1, 2 or 3. Also optionally two or more $R^6$ or $R^7$ groups are joined together in a ring structure.

In more specific embodiments, each $R^3$, $R^4$ and $R^5$ is independently selected from a group consisting of alkyl, substituted alkyl, cycloalkyl, substituted cycloalkyl, heterocycloalkyl, substituted heterocycloalkyl, aryl, substituted aryl, heteroaryl, substituted heteroaryl and silyl. Specific examples of $R^3$, $R^4$ and $R^5$ are methyl, ethyl, propyl, butyl, cyclopentyl, cylcohexyl, cyclooctyl, phenyl, naphthyl, benzyl, trimethylsilyl, and the like.

More specifically, of $R^6$ may be chosen from the group consisting of alkyl, substituted alkyl, cycloalkyl, substituted cycloalkyl, heterocycloalkyl, substituted heterocycloalkyl, aryl, substituted aryl, heteroaryl, substituted heteroaryl, silyl, amino, alkoxy, aryloxy, phosphino, boryl, transition metals, halogens and combinations thereof Specific examples of $R^6$ include methyl, ethyl, propyl, t-butyl, phenyl, methoxy, alkoxy, thioalkyl, cyano, acetyl, benzoyl, nitro, dimethylamino, diethylamino, methylphenylamino, benzylmethylamino, trimethylsilyl, dimethylboryl, diphenylboryl, methylphenylboryl, dimethoxyboryl, chromium tricarbonyl, ruthenium tricarbonyl, and cyclopentadienyl iron. $R^6$ can also be a water-solubilizing group, such as $SO_3G$, where G is Na, K and the like. $R^6$ may also be a transition metal that is eta bonded to the benzene ring in the backbone of the ligand. Optionally, two or more $R^6$ groups combine to form a fused ring structure with the aromatic group that forms a part of the ligand backbone. The additional fused ring may or may not contain a heteroatom. Examples of the aromatic group that is part of the backbone as combined with two or more $R^6$ groups that have formed a fused ring are nathphalene, quinoline, indole and the like.

More specific embodiments of $R^7$ are those where a mono-cyclopentadienyl or bis-cyclopentadienyl metallocene is formed as part of the ligand. Thus, $R^7$ may be a moiety having a metal atom selected from the group consisting of metals from the Periodic Table of Elements, such as Fe, Rh, Mo, Ru, Cr, Zr, Ti, Hf, Co. Specific examples of $R^7$ include FeCp, CrCp and $ZrCpR_2$, where Cp is a substituted or unsubstituted cyclopentadienyl and R is selected from the same group as $R^5$. Throughout this specification, it is intended that the bond between the Cp ring in the ligand and $R^7$ is an $\eta^5$ bond. Thus, formula II may appear to have the structure:

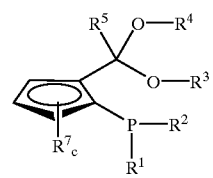

Within this first aspect, particularly preferred ligands are:

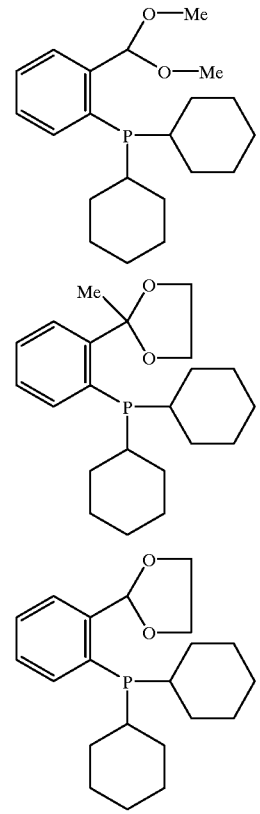

In a second aspect, the ligands of this invention may be characterized by the general formulas:

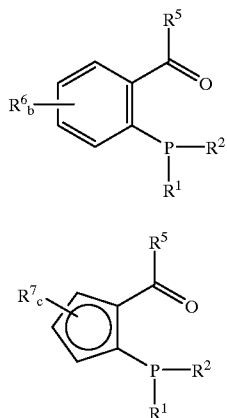

III

IV where $R^1$, $R^2$, $R^5$, $R^6$ $R^7$, b and c have the definitions given above.

A particularly preferred ligand within this second aspect is:

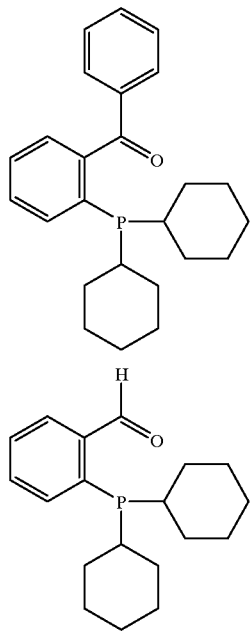

The ligands of this invention may be on a support or not. For example, the support could be any one of the R groups in the formulas I, II, III or IV (i.e., $R^1$, $R^2$, $R^3$, $R^4$, $R^5$, $R^6$ or $R^7$). In that embodiment, the support may be a polymer or functionalized polymer, such as polystyrene. In the case of heterogeneous reactions, the ligands may be supported, with or without the metal coordinated (discussed below), on an organic or inorganic support. Suitable supports include silicas, aluminas, zeolites, polyethyleneglycols, polystyrenes, polyesters, polyamides, peptides and the like.

The desired ligand is typically combined with a metal atom, ion, compound or other metal precursor compound. In many applications, the ligands of this invention will be combined with such a metal compound or precursor and the product of such combination is not determined, if a product forms. For example, the ligand may be added to a reaction vessel at the same time as the metal or metal precursor compound along with the reactants. The metal precursor compounds may be characterized by the general formula $M(L)_n$, (also referred to as $ML_n$ or $M-L_n$) where M is a metal selected from the group consisting of Groups 5, 6, 7, 8, 9 and 10 of the Periodic Table of Elements. In more specific embodiments, M is selected from the group consisting of Ni, Pd, Fe, Pt, Ru, Rh, Co and Ir. L is a ligand chosen from the group consisting of halide, alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, hydroxy, boryl, silyl, hydrido, thio, seleno, phosphino, amino, and combinations thereof. When L is a charged ligand, L is selected from the group consisting of hydrogen, halogens, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, and combinations thereof. When L is a neutral ligand, L is selected from the group consisting of carbon monoxide, isocyanide, nitrous oxide, $PA_3$, $NA_3$, $OA_2$, $SA_2$, $SeA_2$, and combinations thereof, wherein each A is independently selected from a group consisting of alkyl, substituted alkyl, heteroalkyl, cycloalkyl, substituted cycloalkyl, heterocycloalkyl, substituted heterocycloalkyl, aryl, substituted aryl, heteroaryl, substituted heteroaryl, alkoxy, aryloxy, silyl, and amino. Specific examples of suitable metal precursor compounds include $Pd(dba)_2$ (dba=dibenzylydieneacteone), $Pd_2(dba)_3$, $Pd(OAc)_2$ (Ac=acetate), $PdCl_2$, $Pd(TFA)_2$, (TFA= trifluoroacetate), $(CH_3CN)_2PdCl_2$, and the like. In this context, the ligand to metal precursor compound ratio is in the range of about 0.01:1 to about 100:1, more preferably in the range of about 0.5:1 to about 20:1. The metal atom, ion or metal precursor may be supported or not. Supports may be organic or inorganic. Similar to the ligands, the support may be an L. In other embodiments, the support will not form part of the metal precursor and suitable supports include silicas, aluminas, zeolites, polyethyleneglycols, polystyrenes, polyesters, polyamides, peptides and the like. Specific examples of Pd supported metals include Pd/C, $Pd/SiO_2$, $Pd/CaCO_3$, $Pd/BaCO_3$, Pd/aluminate, Pd/aluminum oxide, Pd/polystyrene, although any of the metals listed above could replace Pd in this list, e.g., Ni/C, etc.

In other applications, the ligand will be mixed with a suitable metal precursor compound prior to or simultaneous with allowing the mixture to be contacted to the reactants. When the ligand is mixed with the metal precursor compound, a metal-ligand complex may be formed, which may be a catalyst. Looking at the first ligand aspect of this application, the metal complexes of this invention may be characterized by either of the formulas:

V

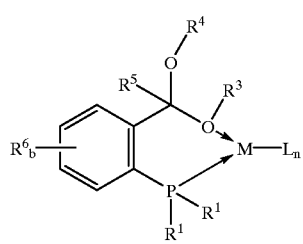

-continued

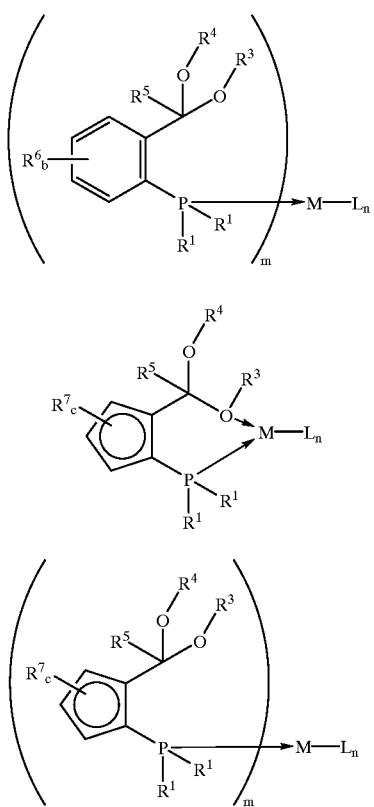

where $R^1$, $R^2$, $R^3$, $R^4$, $R^5$, $R^6$, M, L, b, c and n have the definitions given above and additionally m is a number that is 1, 2 or 3. The single crystal X-ray crystallographic characterization of one such complex by combining one of the above preferred ligands with metal precursor $Pd(dba)_2$ and para-t-butylbromobenzene resulted in a complex having the following structure:

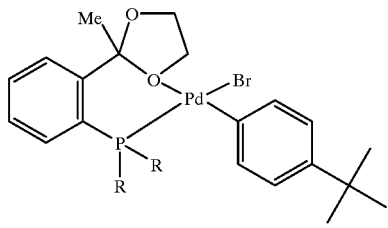

Looking at the second ligand aspect of this invention, the metal complexes of this invention may take the form:

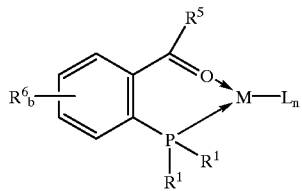

-continued

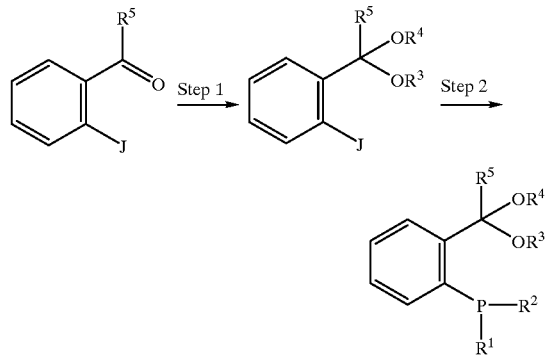

Generally, the ligands of the first aspect of this invention may be prepared by the following schemes. For the ligands within the first aspect, a general scheme is Scheme 1 where each of the variables has the above definition and J is selected from the group consisting of H, Br, I, Cl, F, tosylates, triflates and nonaflates. In scheme 1, step 1 is a standard acetal/ketal formation reaction that is acid-catalyzed in the presence of a suitable alcohol. In scheme 1, step 2 changes depending on J. When J is H or Br, step 2 comprises the addition of a butyl lithium reagent (e.g., n-BuLi or s-BuLi or t-BuLi) followed by addition of $ClPR^1R^2$ or $BrPR^1R^2$. When J is F, step 2 comprises addition of a reagent that is characterized by $M''PR^1R^2$ where M" is either Li, Mg, Zn or K. Finally, when J is Br, I, Cl, a tosylate, a triflate or a nonaflate, step 2 in scheme 1 comprises a metal catalyzed cross-coupling reaction with $M'''PR^1R^2$ where M'" is H, $SiR_3$(with R=alkyl, aryl or cycloalkyl) or M". The catalyst for this step 2 is a suitable metal, such as Pd or Ni, optionally with a ligand. Such step 2 cross coupling reactions are known to those skilled in the art.

A more specific description within scheme 1 for making the ligands is where one starts with 2-bromobenzaldehyde taken up in 100 ml dry benzene in a 250 ml round-bottom flask equipped with a reflux condensor and Dean-Stark apparatus upon which p-toluenesulfonic acid monohydrate and alcohol are added (except that where the alcohol is methanol, methanol was as a reagent and trimethylformate was used as the solvent at 65° C. for 8 hours). The mixture is then heated to reflux with stirring. After cooling to room temperature, the benzene is removed. To the resulting residue is added 200 ml of a saturated aqueous solution of NaHCO$_3$ and extracted with Et$_2$O. The organic extracts are combined and washed with brine, dried over MgSO$_4$, filtered, and concentrated on a rotary evaporator to give the desired acetal which is used in the next step without further purification. The o-dialkoxy-bromobenzene derivatives are dissolved in anhydrous diethyl ether (30 mL) and the solution is cooled to −78 ° C. t-Butyllithium is added dropwise with stirring. The reaction is stirred for 1 hour. A secondary chlorophoshine is added dropwise via a syringe at −78 ° C. with stirring. The reaction mixture is allowed to warm up to room temperature over an additional 18 hours. To the mixture, deoxygenated water is added slowly. The organic phase is separated under argon and the aqueous phase is washed with diethyl ether. The combined organic phase is dried under vacuum at 40° C. The crude product is washed with methanol and dried under vacuum, affording the desired ligands.

For the ligands of the second aspect, a synthesis procedure is as follows:

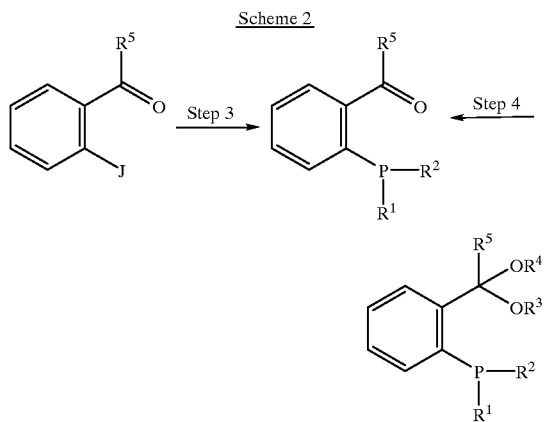

Scheme 2

In scheme 2, the variables are as defined above. As can be seen the ligands of the second aspect can be prepared from the same starting material and following step 3 or by starting with the ligands of the first aspect and following step 4. Step 3 in scheme 2 changes depending on J. When J is H or Br, step 3 comprises the addition of a butyl lithium reagent (e.g., n-BuLi or s-BuLi or t-BuLi) followed by addition of ClPR$^1$R$^2$ or BrPR$^1$R$^2$. When J is F, step 3 comprises addition of a reagent that is characterized by M"PR$^1$R$^2$ where M" is either Li, Mg, Zn or K. Finally, when J is Br, I, Cl, a tosylate, a triflate or a nonaflate, step 3 in scheme 2 comprises a metal catalyzed cross-coupling reaction with M'''PR$^1$R$^2$ where M''' is H, SiR$_3$ (with R=alkyl, aryl or cycloalkyl) or M". The catalyst for this step 3 is a suitable metal, such as Pd or Ni, optionally with a ligand. Such step 3 cross coupling reactions are known to those skilled in the art. When step 4 is being followed, a standard acetal/ketal hydrolysis, acid-catalyzed reaction is run in the presence of water.

The catalyst compositions and metal complexes of this invention catalyze reactions that include activation of and/or formation of H—Si, H—H, H—N, H—O, H—P, H—S, C—H, C—C, C=C, C≡C, C-halogen, C—N, C—O, C—S, C—P, and C—Si bonds. Specifically, such reactions include carbonylation, hydroformylation, hydroxycarbonylation, hydrocarbonylation, hydroesterification, hydrogenation, transfer hydrogenation, hydrosilylation, hydroboration, hydroamination, epoxidation, aziridation, reductive amination, C—H activation, insertion, C—H activation-insertion, C—H activation-substitution C-halogen activation, C-halogen activation-substitution, C-halogen activation-insertion, cyclopropanation, alkene metathesis, alkene oligomerization, alkene polymerization, alkyne oligomerization, alkyne polymerization, co-polymerization, CO-alkene co-oligomerization, CO-alkene co-polymerization, CO-alkyne co-oligomerization and CO-alkyne co-polymerization. These reactions may occur at previously known conditions (or possibly novel conditions). Moreover, these reactions may be homogeneous or heterogeneous.

More specifically, the catalyst compositions and metal complexes of this invention are useful for many metal-catalyzed reactions, particularly for Suzuki cross-coupling reactions with aryl chlorides. In general, this invention may be effectively employed for metal-catalyzed coupling of organometallic reagents with organic electrophiles; metal-catalyzed coupling of organometallic reagents with organic halides; metal-catalyzed coupling of organometallic reagents with aryl halides and vinyl halides; and metal-catalyzed coupling of organometallic reagents with aryl chlorides. In particular, the following reactions can be effectively performed with this invention: aryl-aryl or biaryl coupling reactions, including coupling of aryl boron reagents (aryl boronic acid and esters) with aryl halides including aryl chlorides, aryl triflates, aryl tosylates, aryl mesylates (Suzuki coupling); coupling of aryl zinc reagents with the compounds as above; coupling of aryl magnesium reagents with the compounds as above; coupling of aryl tin reagents with the compounds as above; and coupling of aryl metal reagents with the compounds as above. Those of skill in the art will recognize that this list can be repeated by simply substituting heteroaryl for aryl without departing from the scope of this invention. Additional reactions that can be effectively performed with this invention include vinyl-aryl coupling reactions such as the coupling of vinyl metal reagents with the compounds as above, coupling of vinyl aluminate reagents with the compounds as above, coupling of vinyl cuprate reagents with the compounds as above, coupling of vinyl zirconium reagents with the compounds as above; and the coupling of vinyl boron reagents with the compounds as above. Still further, reactions that can be effectively performed with this invention include reactions which involve oxidative addition, transmetallation and reductive elimination sequence or oxidative addition, insertion or beta-hydride elimnation sequence in the catalytic cycle, including Heck reactions that involve metal-catalyzed olefination of aryl halides including chloride, aryl mesylates, tosylates, aryl triflates. Other reaction examples, include Sonogashira, cyanation, aryl amination, Stille coupling, Castro-Stephens, and hydrogenations.

To carry out the process of this invention for one type of reaction, a first aromatic compound, a second aromatic compound, a base, a catalytic amount of metal precursor and a catalytic amount of the ligand are added to an inert solvent or inert solvent mixture. In a batch methodology, this mixture is stirred at a temperature of from 0° C. to 200° C., preferably at from 30° C. to 170° C., particularly preferably at from 50° C. to 150° C., most particularly preferably at from 60° C. to 120° C., for a period of from 5 minutes to 100 hours, preferably from 15 minutes to 70 hours, particularly preferably from ½ hour to 50 hours, most particularly preferably from 1 hour to 30 hours. After the reaction is complete, the catalyst may be obtained as solid and separated off by filtration. The crude product is freed of the solvent or the solvents and is subsequently purified by methods known to those skilled in the art and matched to the respective product, e.g. by recrystallization, distillation, sublimation, zone melting, melt crystallization or chromatography.

Solvents suitable for the process of the invention are, for example, ethers (e.g., diethyl ether, dimethoxymethane, diethylene glycol, dimethyl ether, tetrahydrofuran, dioxane, diisopropyl ether, tert-butyl methyl ether), hydrocarbons (e.g., hexane, iso-hexane, heptane, cyclohexane, benzene, toluene, xylene), alcohols (e.g., methanol, ethanol, 1-propanol, 2-propanol, ethylene glycol, 1-butanol, 2-butanol, tert-butanol), ketones (e.g., acetone, ethyl methyl ketone, iso-butyl methyl ketone), amides (e.g., dimethylformamide, dimethylacetamide, N-methylpyrrolidone), nitriles (e.g., acetonitrile, propionitrile, butyronitrile), water and mixtures thereof. Particularly preferred solvents are ethers (e.g., dimethoxyethane, tetrahydrofuran), hydrocarbons (e.g., cyclohexane, benzene, toluene, xylene), alcohols (e.g., ethanol, 1-propanol, 2-propanol), water and combinations thereof. Most particularly preferred are dimethoxyethane, benzene, toluene, xylene, dioxane, ethanol, water and combinations thereof.

Bases which are useful in the process of the invention are alkali metal and alkaline earth metal hydroxides, alkali metal and alkaline earth metal carbonates, alkali metal hydrogen carbonates, alkali metal and alkaline earth metal acetates, alkali metal and alkaline earth metal alkoxides, alkali metal and alkaline earth metal phosphates, primary, secondary and tertiary amines, alkali metal and alkaline earth fluorides, and ammonium fluorides. Particularly preferred are alkali metal and alkaline earth metal phosphates, alkali metal and alkaline earth metal carbonates, alkali metal hydrogen carbonates, alkali metal and alkaline earth fluorides, and anunonium fluorides. Most particularly preferred are alkali metal phosphates, such as potassium phosphate. The base is preferably used in the process of the invention in an amount of from about 1 to about 1000 mol %, particularly preferably from about 50 to about 500 mol %, very particularly preferably from about 100 to about 400 mol %, in particular from about 150 to about 300 mol %, based on the aromatic boronic acid.

The metal precursor used is as described above and may be added to the process along with the reactants. The metal portion of the catalyst (metal precursor or metal complex) is used in the process of this invention in a proportion of from about 0.0001 to about 10 mol %, preferably from about 0.1 to about 5 mol %, particularly preferably from about 0.5 to about 3 mol %, most particularly preferably from about 1.0 to about 1.5 mol %, based on the second aromatic compound. The ancillary ligand is used in the process in a proportion of from about 0.0001 to about 20 mol %, preferably from about 0.2 to about 15 mol %, particularly preferably from about 0.5 to about 10 mol %, most particularly preferably from about 1 to about 6 mol %, based on the second aromatic compound. These amounts may be combined to give metal precursor to ligand ratios useful in the process. It is also possible, if desired, to use mixtures of two or more different ligands.

The first aromatic compounds for the process may be characterized by either of the general formulas:

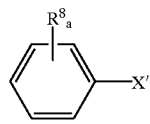

XIII

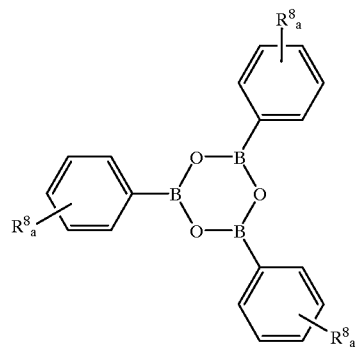

XIV where $R^8$ is seleted from the group consisting of hydrogen, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, and combinations thereof, a is 0, 1, 2, 3, 4 or 5 and optionally two or more $R^8$ groups are joined together in a ring structure; X' is selected from the group consisting of $BR^{10}_2$, $B(OR^{10})_2$, $MgQ^1$, $ZnQ^1$, $CuQ^1$, $SiR^{10}_3$, $SnR^{10}_3$ or Li, wherein each $R^{10}$ is independently selected from the group consisting of hydrogen, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, and combinations thereof; and $Q^1$ is selected from the group consisting of Cl, Br, I or F. See also U.S. Pat. No. 5,756,804, incorporated herein by reference for other, similar formulas. Specific boronic acids that fit this definition of first aromatic compounds are listed in Table 1, below.

The second aromatic compounds for the process of the invention those of the formula:

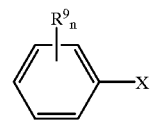

where X is Br, Cl, F, I, tosylates, triflates, or $N_2^+$ and $R^9$ is selected from the group consisting of hydrogen, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, and combinations thereof; and a is 0, 1, 2, 3, 4 or 5. Optionally two or more $R^9$ groups are joined together in a ring structure. Preferable, $R^9$ is selected from the group consisting of methyl, ethyl, methoxy, —CN and —$CF_3$. See also U.S. Pat. No. 5,756,804, incorporated herein by reference for other, similar formulas. Specific compounds that meet fit within the scope of the second aromatic compounds are listed in Table 1.

Products of the process of the invention are polycyclic aromatic compounds having a aryl-aryl bond, having the general structure:

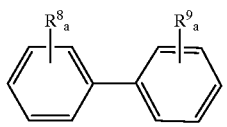

The products are also suitable as precursors for pharmaceuticals, cosmetics, fungicides, herbicides, insecticides, dyes, detergents and polymers, including additives for the same.

EXAMPLES

General. All reactions were performed under an argon atmosphere in oven-dried glass Schlenk tubes using standard Schlenk techniques. All aryl halides, all arnines, sodium t-butoxide, bis(dibenzylideneacetone)palladium, benzene, ethanol, diethyl ether, methylene chloride, toluene, and 1,4-dioxane were purchased from commercial sources and used as such. All solvents were of the anhydrous, sure-seal grade. Column chromatography was performed using commercially available Silica Gel 60 (particle size: 0.063–0.100 mm), hexanes, and ethyl acetate. GCMS analyses were conducted on a Hewlett-Packard 6890 instrument. $^1$H, $^{13}$C, and $^{31}$P NMR spectra were obtained using a Bruker 300 MHz FT-NMR spectrometer using standard frequencies for the different nuclei. Chemical shifts in $^1$H and $^{13}$C NMR spectra were calibrated with reference to the chemical shift of residual protiated solvent. Chemical shifts in $^{31}$P NMR spectra were calibrated with reference to 85% $H_3PO_4$; a negative value of chemical shift denotes resonance upfield from $H_3PO_4$. Coupling constants are reported in Hz. Elemental analyses were performed by E & R Microanalytical Laboratory, Inc., N.J.

Example 1

2-(2'-Dicyclohexylphosphinophenyl)-2-methyl-1,3-dioxolane

(Ligand 1): 2-(2'-bromophenyl)-2-methyl-1,3-dioxolane (2.02 g, 8.31 mmol) was dissolved in anhydrous diethyl ether (30 mL) and the solution was cooled to –78° C. n-Butyllithium (5.7 mL, 1.6 M solution in hexane, 9.13 mmol) was added dropwise with stirring. The reaction was stirred for 2 hours. Chlorodicyclohexylphosphine (2.32 g, 9.96 mmol) was added dropwise via a syringe at –78 ° C. with stirring. The reaction mixture was allowed to warm up to room temperature and stirred for an additional 18 hours. To the reaction mixture was added argon purged water (25 ML) slowly. The organic phase was separated under argon and the aqueous phase was washed with diethyl ether (20 mL). The combined organic phase was concentrated under vacuum to afford a colorless oil, which was crystallized from methanol to afford ligand 1 as a white crystalline solid having the structure shown below (yield: 2.13 g, 71% un-optimized yield). $^{31}$P{$^1$H} NMR (CDCl$_3$): δ–8.2. $^1$H NMR (CDCl$_3$): δ 7.67 (br 1H, ArH), 7.59 (br, 1H, ArH), 7.29 (br, 2H, ArH), 4.02 (m, 2H, —OCH$_2$CH$_2$O—, 3.73 (m, 2H, —OCH$_2$CH$_2$O—), 1.97 - 1.15 (br. m, 25H, CyH and CH$_3$). $^{13}$C NMR (CDCl$_3$): δ 149.3 (d, J$_{PC}$=23), 134.8 (d, J$_{PC}$=28), 134.0, 128.0, 127.1, 125.4 (d, J$_{PC}$=6), 109.6 (—OCO—), 64.0 (—OCH$_2$—), 36.3 (d, J$_{PC}$=15), 30.8 (d, J$_{PC}$=18), 30.0 (d, J$_{PC}$=11), 29.4 (d, J$_{PC}$=14), 27.4 (d, J$_{PC}$=9), 27.2 (d, J$_{PC}$=12), 26.4. Anal. for C$_{22}$H$_{33}$O$_2$P; Calcd: C, 73.30; H, 9.23; P, 8.59; Found: C, 73.50; H, 9.46; P, 8.36.

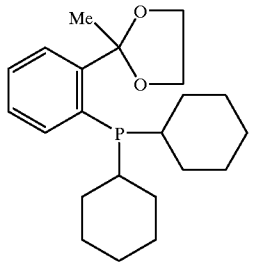

Ligand 1

Examples 2–8

General Procedure for Pd(dba)$_2$/Ligand 1-catalyzed reaction of aryl chlorides with boronic acid derivatives listed in Table 1:

A mixture of aryl chloride (1.0 mmol), aryl boronic acid (1.5 mmol), CsF (3.0 mmol) or K$_3$PO$_4$ (2.0 mmol), Pd(dba)$_2$ (0.005–0.02 mmol), ligand 1 (0.015–0.06 mmol) in 1,4-dioxane (4 ml) was heated to 80° C. or 100° C. The reaction was monitored by GC/MS. The details of the reaction conditions and results are summarized in Table 1.

TABLE 1

Examples of Suzuki Reactions

| Example | Aryl Chloride | Boronic acid | Temp °C. | % Pd | Product | Yield % |
|---|---|---|---|---|---|---|
| 2 | F$_3$C—⬡—Cl | ⬡—B(OH)$_2$ | 80 | 0.5 | F$_3$C—⬡—⬡ | 92 |
| 3 | F$_3$C—⬡—Cl | F$_3$C—⬡—B(OH)$_2$ | 100 | 1.0 | F$_3$C—⬡—⬡—CF$_3$ | 94 |

TABLE 1-continued

Examples of Suzuki Reactions

| Example | Aryl Chloride | Boronic acid | Temp °C. | % Pd | Product | Yield % |
|---|---|---|---|---|---|---|
| 4 | o-Cl-acetophenone | 4-Me-C6H4-B(OH)2 | 100 | 1.0 | 2-acetyl-4'-methylbiphenyl | 96 |
| 5 | 6-chloro-1,3-benzodioxole | 2-naphthyl-B(OH)2 | 100 | 1.0 | 6-(2-naphthyl)-1,3-benzodioxole | 90 |
| 6 | 3-chloro-anisole | 4-CF3-C6H4-B(OH)2 | 100 | 1.0 | 3-methoxy-4'-trifluoromethylbiphenyl | 93 |
| 7 | 3,5-dimethyl-chlorobenzene | phenyl-B(OH)2 | 100 | 1.0 | 3,5-dimethylbiphenyl | 88 |
| 8 | 2-chlorobenzonitrile | phenyl-B(OH)2 | 100 | 1.0 | 2-cyanobiphenyl | 91 |

Example 9

1-(2'-Dicyclohexylphosphinophenyl)-1,1-dimethoxymethane (Ligand 2): o-Dimethoxymethyl-bromobenzene (4.13 g, 17.9 mmol) was dissolved in anhydrous diethyl ether (60 mL) and the solution was cooled to −78° C. t-Butyllithium (21.2 mL, 1.7 M solution in hexane, 36 mmol) was added dropwise with stirring. The reaction was stirred for 1 hour. Chlorodicyclohexylphosphine (5.0 g, 21.5 mmol) was added dropwise via a syringe at −78° C. with stirring. The reaction mixture was allowed to warm up to room temperature over an additional 18 hours. To the mixture was added deoxygenated water (40 mL) slowly. The organic phase was separated under argon and the aqueous phase was washed with diethyl ether (20 mL). The combined organic phase was dried under vacuum at 40° C. The crude product was washed with methanol (3×10 mL) and dried under vacuum, affording ligand 2 as a white solid product, having the structure shown below (Yield: 5.66 g, 90.7%). $^{31}P\{^1H\}$ (CDCl$_3$): δ−18.5. $^1H$ NMR (CDCl$_3$): δ7.62 (br, 1H, ArH), 7.40 (br, 1H, ArH), 7.25 (m, 2H, ArH), 6.17 (d, $J_{PH}$=6.5, 1H CH(OCH$_3$)$_2$), 3.35 (s, 6H,—OCH$_3$), 2.0 - 0.9 (m, 22H, CyH). $^{13}C\{^1H\}$ NMR (CDCl$_3$): δ 144.8 (d, $J_{PC}$=22), 134.3 (d, $J_{PC}$=25), 132.3, 128.5, 127.5, 126.2 (d, $J_{PC}$=5), 101.8 (d, $J_{PC}$=29), 53.8, 34.2 (d, $J_{PC}$=12), 30.3 (d, $J_{PC}$=17), 29.3 (d, $J_{PC}$=9), 27.0 (m, 2C), 26.2. Anal. For C$_{21}$H$_{33}$ $_{O2}$P; Calcd: C, 72.38; H, 9.55; P, 8.89; Found: C, 72.46; H, 9.90; P, 9.03.

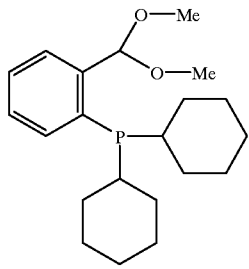

Ligand 2

Example 10

7.65 mg of Pd$_2$(dba)$_3$ (8.35 μmol) and 11.60 mg of Ligand 2 (33.33μmol) were combined in 5 ml of solvent (dioxane, toluene, or 2-propanone) and stirred at room temperature for 2 hours to form a catalyst solution that was used in this example and other examples. CsF (2.28 g, 15.0 mmol), 2-chlorobenzonitrile (0.689 g, 5.00 mmol), and p-tolueneboronic acid (0.748 g, 5.50 mmol) were taken up in 14 ml of dry dioxane under nitrogen and a 0.1 mol % aliquot from the catalyst solution (in dioxane) was added. The mixture was then heated to 80° C. for 12 hours. The mixture was then cooled to room temperature, diluted with Et$_2$O, and extracted with a saturated NH$_4$Cl solution (3×20 ml). The Et$_2$O layer was dried over MgSO$_4$, filtered and concentrated to give a viscous oil which was purified by flash chromatography to give 844 mg of 2-cyano-4'-methylbiphenyl in 87% isolated yield.

Example 11

NaF (0.126 g, 3.00 mmol), 2-chlorobenzonitrile (0.138 g, 1.00 mmol), and p-tolueneboronic acid (0.143 g, 1.05 mmol) were taken up in 2 ml of dry toluene under nitrogen and a 0.1 mol % aliquot from the catalyst solution (in toluene) from Example 10 was added. The mixture was then heated to 80° C. and monitored by GC/MS. After 1 hour, GC/MS analysis showed a conversion of <1% based on the disappearance of 2-chlorobenzonitrile.

Example 12

K$_3$PO$_4$ (0.638 g, 3.00 mmol), 2-chlorobenzonitrile (0.138 g, 1.00 mmol), and p-tolueneboronic acid (0.143 g, 1.05 mmol) were taken up in 2 ml of dry toluene under nitrogen and a 0.1 mol % aliquot from the catalyst solution (in toluene) from Example 10 was added. The mixture was then heated to 80° C. and monitored by GC/MS. After 1 hour, GC/MS analysis showed a conversion of 43% based on the disappearance of 2-chlorobenzonitrile and a selectivity of >99.03% for the desired product 2-cyano-4'-methylbiphenyl over 4,4'-dimethylbiphenyl. After 12 hours, GC/MS analysis showed a conversion of 65% based on the disappearance of 2-chlorobenzonitrile and a selectivity of >99.46% for the desired product 2-cyano-4'-methylbiphenyl over 4,4'-dimethylbiphenyl.

Example 13

K$_2$CO$_3$ (0.415 g, 3.00 mmol), 2-chlorobenzonitrile (0.138 g, 1.00 mmol), and p-tolueneboronic acid (0.143 g, 1.05 mmol) were taken up in 2 ml of dry toluene under nitrogen and a 0.1 mol % aliquot from the catalyst solution (in toluene) from Example 10 was added. The mixture was then heated to 80° C. and monitored by GC/MS. After 1 hour, GC/MS analysis showed a conversion of 52% based on the disappearance of 2-chlorobenzonitrile and a selectivity of >99.26% for the desired product 2-cyano-4'-methylbiphenyl over 4,4'-dimethylbiphenyl. After 12 hours, GC/MS analysis showed a conversion of 73% based on the disappearance of 2-chlorobenzonitrile and a selectivity of >99.45% for the desired product 2-cyano-4'-methylbiphenyl over 4,4'-dimethylbiphenyl.

Example 14

Na$_2$CO$_3$ (0.318 g, 3.00 mmol), 2-chlorobenzonitrile (0.138 g, 1.00 mmol), and p-tolueneboronic acid (0.143 g, 1.05 mmol) were taken up in 2 ml of dry toluene under nitrogen and a 0.1 mol % aliquot from the catalyst solution (in toluene) from Example 10 was added. The mixture was then heated to 80° C. and monitored by GC/MS. After 1 hour, GC/MS analysis showed a conversion of 9% based on the disappearance of 2-chlorobenzonitrile and a selectivity of >98.88% for the desired product 2-cyano-4'-methylbiphenyl over 4,4'-dimethylbiphenyl. After 12 hours, GC/MS analysis showed a conversion of 16% based on the disappearance of 2-chlorobenzonitrile and a selectivity of >96.76% for the desired product 2-cyano-4'-methylbiphenyl over 4,4'-dimethylbiphenyl.

Example 15

NaF (0.126 g, 3.00 mmol), 2-chlorobenzonitrile (0.138 g, 1.00 mmol), and p-tolueneboronic acid (0.143 g, 1.05 mmol) were taken up in 2 ml of dry toluene under nitrogen and a 0.1 mol % aliquot from the catalyst solution (in toluene) from Example 10 was added followed by the addition of 1 ml distilled H$_2$O. The mixture was then heated to 80° C. and monitored by GC/MS. After 1 hour, GC/MS analysis showed a conversion of 11% based on the disappearance of 2-chlorobenzonitrile and a selectivity of >96.55 % for the desired product 2-cyano-4'-methylbiphenyl over 4,4'-dimethylbiphenyl.

Example 16

K$_3$PO$_4$ (0.638 g, 3.00 mmol), 2-chlorobenzonitrile (0.138 g, 1.00 mmol), and p-tolueneboronic acid (0.143 g, 1.05 mmol) were taken up in 2 ml of dry toluene under nitrogen and a 0.1 mol % aliquot from the catalyst solution (in toluene) from Example 10 was added followed by the addition of 1 ml distilled H$_2$O. The mixture was then heated to 80° C. and monitored by GC/MS. After 1 hour, GC/MS analysis showed a conversion of 19% based on the disappearance of 2-chlorobenzonitrile and a selectivity of >98.56% for the desired product 2-cyano-4'-methylbiphenyl over 4,4'-dimethylbiphenyl. After 12 hours, GC/MS analysis showed a conversion of 20% based on the disappearance of 2-chlorobenzonitrile and a selectivity of >98.87% for the desired product 2-cyano-4'-methylbiphenyl over 4,4'-dimethylbiphenyl.

Example 17

K$_2$CO$_3$ (0.415 g, 3.00 mmol), 2-chlorobenzonitrile (0.138 g, 1.00 mmol), and p-tolueneboronic acid (0.143 g, 1.05 mmol) were taken up in 2 ml of dry toluene under nitrogen and a 0.1 mol % aliquot from the catalyst solution (in toluene) from Example 10 was added followed by the addition of 1 ml distilled H$_2$O. The mixture was then heated to 80° C. and monitored by GC/MS. After 1 hour, GC/MS analysis showed a conversion of 24% based on the disappearance of 2-chlorobenzonitrile and a selectivity of >98.60% for the desired product 2-cyano-4'-methylbiphenyl over 4,4'-dimethylbiphenyl. After 12 hours, GC/MS analysis showed a conversion of 26% based on the disappearance of 2-chlorobenzonitrile and a selectivity of >99.26% for the desired product 2-cyano-4'-methylbiphenyl over 4,4'-dimethylbiphenyl.

Example 18

Na$_2$CO$_3$ (0.318 g, 3.00 mmol), 2-chlorobenzonitrile (0.138 g, 1.00 mmol), and p-tolueneboronic acid (0.143 g, 1.05 mmol) were taken up in 2 ml of dry toluene under nitrogen and a 0.1 mol % aliquot from the catalyst solution (in toluene) from Example 10 was added followed by the addition of 1 ml distilled H$_2$O. The mixture was then heated to 80° C. and monitored by GC/MS. After 1 hour, GC/MS analysis showed a conversion of 27% based on the disappearance of 2-chlorobenzonitrile and a selectivity of >99.28% for the desired product 2-cyano-4'-methylbiphenyl over 4,4'-dimethylbiphenyl. After 12 hours, GC/MS analysis showed a conversion of 31% based on the disappearance of 2-chlorobenzonitrile and a selectivity of >99.11% for the desired product 2-cyano-4'-methylbiphenyl over 4,4'-dimethylbiphenyl.

Example 19

NaF (0.126 g, 3.00 mmol), 2-chlorobenzonitrile (0.138 g, 1.00 mmol), and p-tolueneboronic acid (0.143 g, 1.05 mmol) were taken up in 2 ml of dry 2-butanone under nitrogen and a 0.1 mol % aliquot from the catalyst solution (in 2-butanone) from Example 10 was added. The mixture was then heated to 80° C. and monitored by GC/MS. After 1 hour, GC/MS analysis showed a conversion of 2% based on the disappearance of 2-chlorobenzonitrile and a selectivity of >99.50% for the desired product 2-cyano-4'-methylbiphenyl over 4,4'-dimethylbiphenyl. After 12 hours, GC/MS analysis showed a conversion of 46% based on the disappearance of 2-chlorobenzonitrile and a selectivity of >99.20% for the desired product 2-cyano-4'-methylbiphenyl over 4,4'-dimethylbiphenyl.

Example 20

$K_3PO_4$ (0.638 g, 3.00 mmol), 2-chlorobenzonitrile (0.138 g, 1.00 mmol), and p-tolueneboronic acid (0.143 g, 1.05 mmol) were taken up in 2 ml of dry 2-butanone under nitrogen and a 0.1 mol % aliquot from the catalyst solution (in 2-butanone) from Example 10 was added. The mixture was then heated to 80° C. and monitored by GC/MS. After 1 hour, GC/MS analysis showed a conversion of 63% based on the disappearance of 2-chlorobenzonitrile and a selectivity of >99.53% for the desired product 2-cyano-4'-methylbiphenyl over 4,4'-dimethylbiphenyl. After 12 hours, GC/MS analysis showed a conversion of >99% based on the disappearance of 2-chlorobenzonitrile and a selectivity of >99.28% for the desired product 2-cyano-4'-methylbiphenyl over 4,4'-dimethylbiphenyl.

Example 21

$K_2CO_3$ (0.415 g, 3.00 mmol), 2-chlorobenzonitrile (0.138 g, 1.00 mmol), and p-tolueneboronic acid (0.143 g, 1.05 mmol) were taken up in 2 ml of dry 2-butanone under nitrogen and a 0.1 mol % aliquot from the catalyst solution (in 2-butanone) from Example 10 was added. The mixture was then heated to 80° C. and monitored by GC/MS. After 1 hour, GC/MS analysis showed a conversion of 38% based on the disappearance of 2-chlorobenzonitrile and a selectivity of >99.15% for the desired product 2-cyano-4'-methylbiphenyl over 4,4'-dimethylbiphenyl. After 12 hours, GC/MS analysis showed a conversion of >99% based on the disappearance of 2-chlorobenzonitrile and a selectivity of >99.29% for the desired product 2-methylbiphenyl over 4,4'-dimethylbiphenyl.

Example 22

$Na_2CO_3$ (0.318 g, 3.00 mmol), 2-chlorobenzonitrile (0.138 g, 1.00 mmol), and p-tolueneboronic acid (0.143 g, 1.05 mmol) were taken up in 2 ml of dry 2-butanone under nitrogen and a 0.1 mol % aliquot from the catalyst solution (in 2-butanone) from Example 10 was added. The mixture was then heated to 80° C. and monitored by GC/MS. After 1 hour, GC/MS analysis showed a conversion of 25% based on the disappearance of 2-chlorobenzonitrile and a selectivity of >99.18% for the desired product 2-cyano-4'-methylbiphenyl over 4,4'-dimethylbiphenyl. After 12 hours, GC/MS analysis showed a conversion of 56% based on the disappearance of 2-chlorobenzonitrile and a selectivity of >99.06% for the desired product 2-cyano-4'-methylbiphenyl over 4,4'-dimethylbiphenyl.

Example 23

This is a synthesis of Ligand 3, whose structure is shown below. Dicyclohexylphosphine (0.25 ml, 1.26 mmol) was added to a mixture of 2'-bromobenzophenone (261 mg, 1 mmol), NaO$^t$Bu (115 mg, 1.2 mmol), Pd(dba)$_2$ (12 mg, 0.02 mmol) in o-xylene (4 mL). The mixture was heated from 85° C. to 140 ° C. within 30 min. GC-MS analysis indicated complete consumption of the 2-bromobenzophenone starting material. The reaction mixture was passed through a short silica column (Aldrich 2g $SiO_2$ column) and the column was washed with toluene, yellow solution was obtained. The solution was concentrated under vacuum and MeOH (0.3 ml) was added resulting in the formation of a pale yellow precipitate. After filtration, the solid was further washed with MeOH (4×0.3 ml) and dried under vacuum, yielding the desired ligand 3 as a pale yellow solid (150 mg, 40%). The yield was not optimized. $^{31}P\{^1H\}$ NMR (CDCl$_3$): δ−8.6.

Example 24

This is a synthesis of Ligand 4, shown below. Ligand 4 was prepared from 2-bromoacetophenone by using the experimental procedure described above in Example 23. $^{31}P\{^1H\}$ NMR (CDCl$_3$): δ−6.2.

Example 25

This is a synthesis of Ligand 5, shown below. A reaction mixture of 1-(2'-Dicyclohexylphosphinophenyl)-1,1-dimethoxymethane (ligand 2, 1.0 g, 2.9 mmol), deoxygenated water (5 mL), and p-toluenesulfonic acid monohydrate (55 mg, 0.29 mmol) in THF (10 mL) was stirred at 50–55° C. for 20 hours. The reaction was cooled to 5 ambient temperature and extracted with diethyl ether (2×5 mL). The organic phase was concentrated under vacuum, affording a yellow oil. The crude product was purified by column chromatography on silica gel using hexanes:ethyl acetate (8:1) as the eluent to afford o-dicyclohexylphosphinobenzaldehyde (ligand 5) as a yellow oil (Yield: 740 mg, 85 %). $^{31}P\{^1H\}$ NMR (CDCl$_3$): δ−20.5.

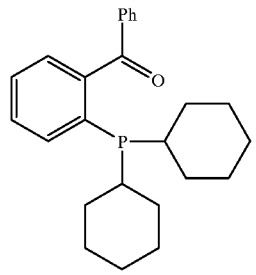

Ligand 3

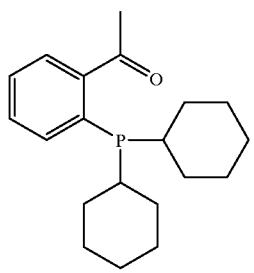

Ligand 4

Ligand 5

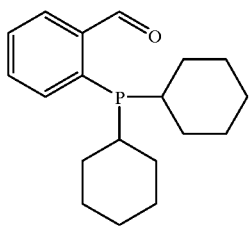

Examples 26–32

General procedure for Pd(dba)₂/ligand 3 & 5 - catalyzed Suzuki reaction of p-toluylboronic acid with 2-chlornbenzonitrile:

Solvent(s) were added to a solid mixture of 2-chlorobenzonitrile (230–305 mg, 1.7–2.2 mmol), p-toluylboronic acid (329 mg), Pd(dba)₂ (1mg), base (1.8–3 equiv.) and ligand (5–7 mg) under argon. Toluene (3 ml) was added to the solid mixture first and H₂O (distilled, 1 ml) was added afterwards in cases where toluene and H₂O were used as solvents (see Table 2). The reaction mixture was heated at 85–90° C. unless indicated otherwise (Table 2). The reactions were analyzed by GC-MS. Details are provided in Table 2. Selectivity to the desired product are >98% in all examples. Conversions are based on relative intensities of the starting material 2-chlorobenzonitrile and product 2-cyano-4'-methylbiphenyl signals and for the disappearance of 2-chlorobenzonitrile. It should be noted that the response factors for the product and starting material are different and the conversion numbers in Table 2 are not corrected for those differences. In Table 2, below, The following abbreviations apply: C or Cat=catalyst; Ar =2-chlorobenzonitrile; Conv.=conversion; L3=Ligand 3; and L5=Ligand 5. For all examples other than example 9, the reactions were analyzed by GC-MS at the two times listed under the reaction time iving the two conversion numbers.

TABLE 2

| Example | Cat | [C]/[Ar] Ratio | Base | [Base]/[Ar] Ratio | Solvent | Reaction Time | Conv. |
|---|---|---|---|---|---|---|---|
| 26 | Pd/L3 | 0.001 | CsF | 1.8 | Toluene | 1 h | 79 |
|  |  |  |  |  |  | 2 h 50 min | 100 |
| 27 | Pd/L3 | 0.001 | CsF | 1.8 | 1,4-dioxane | 1 h | 79 |
|  |  |  |  |  |  | 2 h 50 min | >95 |
| 28 | Pd/L3 | 0.001 | Na₂CO₃ | 3 | Tol/H₂O (3:1) | 1 h | 41 |
|  |  |  |  |  |  | 2 h | 73 |
| 29 | Pd/L3 | 0.001 | K₃PO₄ | 2 | Tol/H₂O (3:1) | 1 h | 73 |
| 30 | Pd/L3 | 0.0001 | CsF | 1.8 | 1,4-dioxane | 0.5 h | 0 |
|  |  |  |  |  |  | 13.5 h | 33 |
| 31 | Pd/L5 | 0.001 | Na₂CO₃ | 3 | Tol/H₂O (3:1) | 1 h | 0 |
|  |  |  |  |  |  | 4 h | 83 |
| 32 | Pd/L5 | 0.001 | CsF | 3 | 1,4-dioxane | 2 h | 90 |
|  |  |  |  |  |  | 2.5 h | 100 |

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated herein by reference for all purposes.

What is claimed is:

1. A ligand characterized by one of the general formulas:

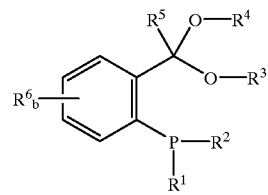

I

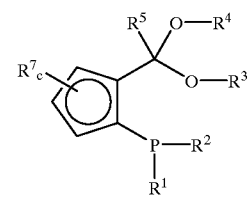

II wherein each $R^1$ and $R^2$ is independently selected from the group consisting of alkyl, substituted alkyl, cycloalkyl and substituted cycloalkyl;

each $R^3$, $R^4$ and $R^5$ is independently selected from the group consisting of hydrogen, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, and combinations thereof; and optionally, $R^3$ and $R^4$ are joined together in a ring structure;

each $R^6$ and $R^7$ is independently selected from the group consisting of hydrogen, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, water solubilizing groups, transition metals and combinations thereof; b is 0, 1, 2, 3 or 4; c is 0, 1, 2 or 3; and optionally two or more $R^6$ or $R^7$ groups are joined together in a ring structure.

2. The ligand of claim 1, wherein each $R^1$ and $R^2$ is independently selected from the group consisting of alkyl, substituted alkyl and cycloalkyl.

3. The ligand of claim 2, wherein each $R^1$ and $R^2$ is cyclohexyl.

4. The ligand of claim 1, wherein each $R^3$ and $R^4$ is independently selected from the group alkyl, substituted alkyl, cycloalkyl and substituted cycloalkyl.

5. The ligand of claim 1, wherein each of $R^3$ and $R^4$ is methyl.

6. The ligand of claim 1, wherein $R^3$ and $R^4$ are joined together in a ring structure with both oxygen atoms and the carbon atom in the backbone of the ligand so that there are between 5 and 20 atoms in said ring.

7. The ligand of claim 6, wherein there are five atoms in said ring and each of $R^3$ and $R^4$ is a methylene.

8. A ligand characterized by one of the general formulas:

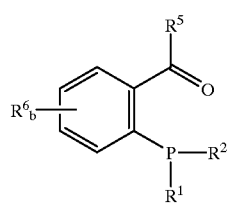

III

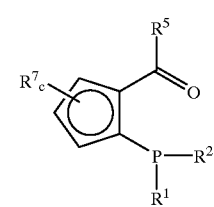

IV wherein each $R^1$ and $R^2$ is independently selected from the group consisting of alkyl, substituted alkyl, cycloalkyl and substituted cycloalkyl;

$R^5$ is selected from the group consisting of hydrogen, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, and combinations thereof; and optionally, $R^3$ and $R^4$ are joined together in a ring structure;

each $R^6$ and $R^7$ is independently selected from the group consisting of hydrogen, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, water solubilizing groups, transition metals and combinations thereof; b is 0, 1, 2, 3 or 4; c is 0, 1, 2 or 3; and optionally two or more $R^6$ or $R^7$ groups are joined together in a ring structure.

9. The ligand of claim 8, wherein each $R^1$ and $R^2$ is independently selected from the group consisting of alkyl, substituted alkyl and cycloalkyl.

10. The ligand of claim 9, wherein each $R^1$ and $R^2$ is cyclohexyl.

11. The ligand of claim 9, wherein $R^5$ is selected from the group hydrogen, alkyl, substituted alkyl, cycloalkyl, substituted cycloalkyl, aryl and substituted aryl.

12. The ligand of claim 11, wherein $R^5$ is hydrogen.

13. The ligand of claim 11, wherein $R^5$ is aryl or substituted aryl.

14. The ligand of claim 13, wherein $R^5$ is phenyl.

15. A composition of matter comprising the ligand of claim 1 and a metal precursor characterized by the general formula $M(L)_n$, where M is a transition metal selected from the group consisting of Pd, Ni, Fe, Co, Ru, Ir and Pt; L is independently each occurrence, a ligand; and n is a number 0, 1, 2, 3, 4, and 5.

16. A composition of matter comprising the ligand of claim 8 and a metal precursor characterized by the general formula $M(L)_n$, where M is a transition metal selected from the group consisting of Pd, Ni, Fe, Co, Ru, Ir and Pt; L is independently each occurrence, a ligand; and n is a number 0, 1, 2, 3, 4, and 5.

17. A reaction comprising contacting the composition of claim 15 with a compound to activate or form H—Si, H—H, H—N, H—O, H—P, H—S, C—H, C—C, C=C, C≡C, C-halogen, C—N, C—O, C—S, C—P, C—B, or C—Si bonds.

18. The reaction of claim 17, wherein the reaction involves C—H, C—C, C—N, C—O, C—S, C—P, C—B and C—Si bond formation.

19. The reaction of claim 18, wherein the reaction is a Suzuki cross-coupling reaction.

20. A reaction comprising contacting the composition of claim 16 with a compound to activate or form H—Si, H—H, H—N, H—O, H—P, H—S, C—H, C—C, C=C, C≡C, C-halogen, C—N, C—O, C—S, C—P, C—B, C—Si bonds.

21. The reaction of claim 20, wherein the reaction involves C—H, C—C, C—N, C—O, C—S, C—P, C—B and C—Si bond formation.

22. The reaction of claim 21, wherein the reaction is a Suzuki cross-coupling reaction.

23. A process for preparing polycyclic aromatic compounds by cross-coupling of a first aromatic compound with a second aromatic compounds in the presence of a base, a solvent, a metal precursor and a ligand that is characterized by any of the following formulas:

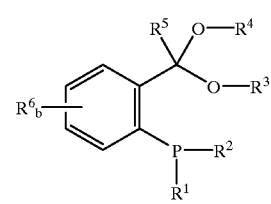

I

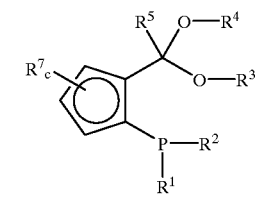

II

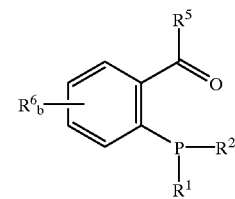

III

-continued

IV

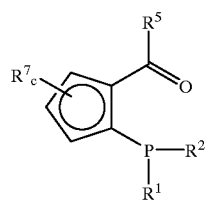

wherein each $R^1$ and $R^2$ is independently selected from the group consisting of alkyl, substituted alkyl, cycloalkyl and substituted cycloalkyl;

each $R^3$, $R^4$ and $R^5$ is independently selected from the group consisting of hydrogen, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, and combinations thereof; and optionally, $R^3$ and $R^4$ are joined together in a ring structure;

each $R^6$ and $R^7$ is independently selected from the group consisting of hydrogen, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, water solubilizing groups, transition metals and combinations thereof; b is 0, 1, 2, 3 or 4; c is 0, 1, 2 or 3; and optionally two or more $R^6$ or $R^7$ groups are joined together in a ring structure.

24. The process of claim 23, wherein each $R^1$ and $R^2$ is independently selected from the group consisting of alkyl, substituted alkyl and cycloalkyl.

25. The process of claim 24, wherein each $R^1$ and $R^2$ is cyclohexyl.

26. The process of claim 23, wherein said base is selected from the group consisting of alkali metal and alkaline earth metal hydroxides, alkali metal and alkaline earth metal carbonates, alkali metaydrogen carbonates, alkali metal and alkaline earth metal acetates, alkali metal and alkaline earth metal alkoxides, alkali metal and alkaline earth metal phosphates, alkali metal and alkaline earth fluorides, ammonium fluorides and primary, secondary and tertiary amines.

27. The process of claim 23, wherein said solvent is selected from the group consisting of ethers, hydrocarbon alcohols, ketones, amides, nitrites, water and mixtures thereof.

28. The process of claim 23, wherein said first aromatic compound is a compound that is characterized by either of the general formulas:

XIII

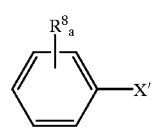

XIV

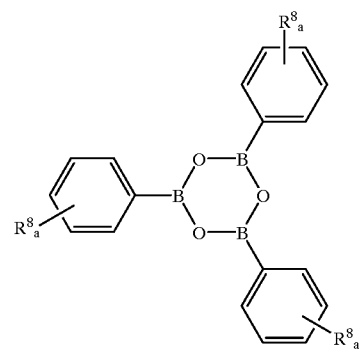

where $R^8$ is selected from the group consisting of hydrogen, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, and combinations thereof; a is 0, 1, 2, 3, 4 or 5 and optionally two or more $R^8$ groups are joined together in a ring structure; X'is selected from the group consisting of $BR^{10}_2$, $B(OR^{10})_2$, $MgQ^1$, $ZnQ^1$, $CuQ^1$, $SiR^{10}_3$ $SnR^{10}_3$ or Li, wherein each $R^{10}$ is independently selected from the group consisting of hydrogen, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, and combinations thereof, and $Q^1$ is selected from the group consisting of Cl, Br, I or F.

29. The process of claim 23, wherein said second aromatic compound is selected from the group consisting of compounds that are characterized by the general formula:

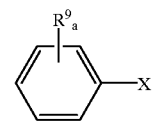

where X is Br, Cl, F, I, tosylates, triflates, or $N_2^{30}$ and each $R^9$ is selected from the group consisting of hydrogen, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, and combinations thereof, and a is 0, 1, 2, 3, 4 or 5; and optionally two or more $R^9$ groups are joined together in a ring structure.

30. The process of claim 23 wherein the aromatic boronic compound is p-tolueneboronic acid and the aromatic halogen compound is o-chlorobenzonitrile.

* * * * *

UNITED STATES PATENT AND TRADEMARK OFFICE
CERTIFICATE OF CORRECTION

PATENT NO.   : 6,124,476
DATED        : September 26, 2000
INVENTOR(S)  : Guram et al.

It is certified that error appears in the above-identified patent and that said Letters Patent is hereby corrected as shown below:

Column 29,
Line 42, the word "metaydrogen" should be replaced with the words
-- metal hydrogen --
Line 48, an -- s -- should be added at the end of the word "hydrocarbon"
Line 49, the word "nitrites" should be replaced with the word -- nitriles --

Column 30,
Line 27, a space should be inserted between "X' " and "is"
Line 48, "30" should be replaced with the sign -- + --

Signed and Sealed this

Third Day of September, 2002

Attest:

JAMES E. ROGAN
Attesting Officer          Director of the United States Patent and Trademark Office